United States Patent [19]

Weber et al.

[11] 4,358,424
[45] Nov. 9, 1982

[54] EQUILIBRATING INSTRUMENT FOR PREPARING QUALITY CONTROL SOLUTIONS

[75] Inventors: Russell S. Weber, Westlake Village; Thomas H. Miller, Newbury Park; Alfons von den Stemmen, Malibu, all of Calif.

[73] Assignee: R. S. Weber, Inc., Westlake, Calif.

[21] Appl. No.: 317,554

[22] Filed: Nov. 2, 1981

[51] Int. Cl.[3] .................. G01N 33/50; G01N 33/96
[52] U.S. Cl. ............................. 422/68; 23/230 B; 23/928; 55/37; 422/50; 422/99
[58] Field of Search ............... 55/37; 23/928, 230 B; 422/50, 68, 99

[56] References Cited

U.S. PATENT DOCUMENTS

| D. 264,504 | 5/1982 | Weber et al. | 23/928 X |
|---|---|---|---|
| 3,127,254 | 3/1964 | Astrup et al. | 55/37 X |
| 3,639,829 | 2/1972 | Harnoncourt | 23/928 X |
| 3,884,640 | 5/1975 | Lock et al. | 422/68 |
| 4,251,483 | 2/1981 | Carroll | 23/928 X |
| 4,256,461 | 3/1981 | Wallace et al. | 23/230 B |
| 4,301,117 | 11/1981 | Smernoff | 23/230 B |

Primary Examiner—Arthur D. Kellogg
Attorney, Agent, or Firm—Ralph B. Pastoriza

[57] ABSTRACT

An improved instrument for preparing quality control solutions of liquid and gas for use in calibrating blood gas analyzers includes a gas inlet providing gas to a humidifier, a diffusion tube, flexible tubing connecting the gas from the humidifier to the diffusion tube and a temperature controlled environment for the diffusion tube. These standard components are arranged in a unique combination permitting the tubing connecting the outlet of the humidifier to the diffusion tube and the diffusion tube itself to both be replaced or individually replaced without disturbing the other components of the instrument. For this purpose, a metal heat block is used as the temperature controlled environment and is provided with an open top for receiving the diffusion tube. The humidifier and connecting tubing are exterior of the heat block so that the referred to replacement of the tubing can readily be carried out. In the preferred embodiment, three cavities are provided in the heat block for holding three individual diffusion tubes there being provided additional gas inlets and humidifiers so that additional quality control solutions can be simultaneously prepared.

8 Claims, 6 Drawing Figures

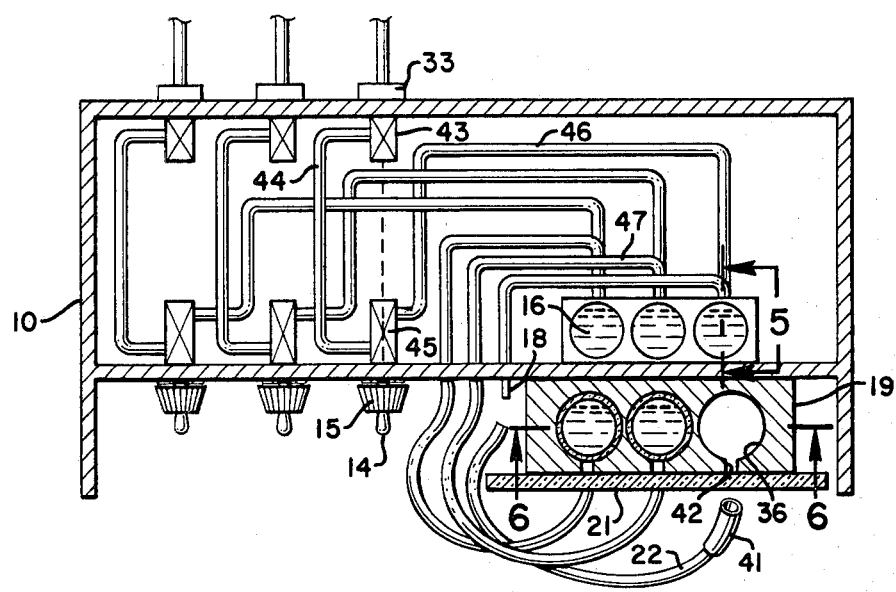
FIG. 4
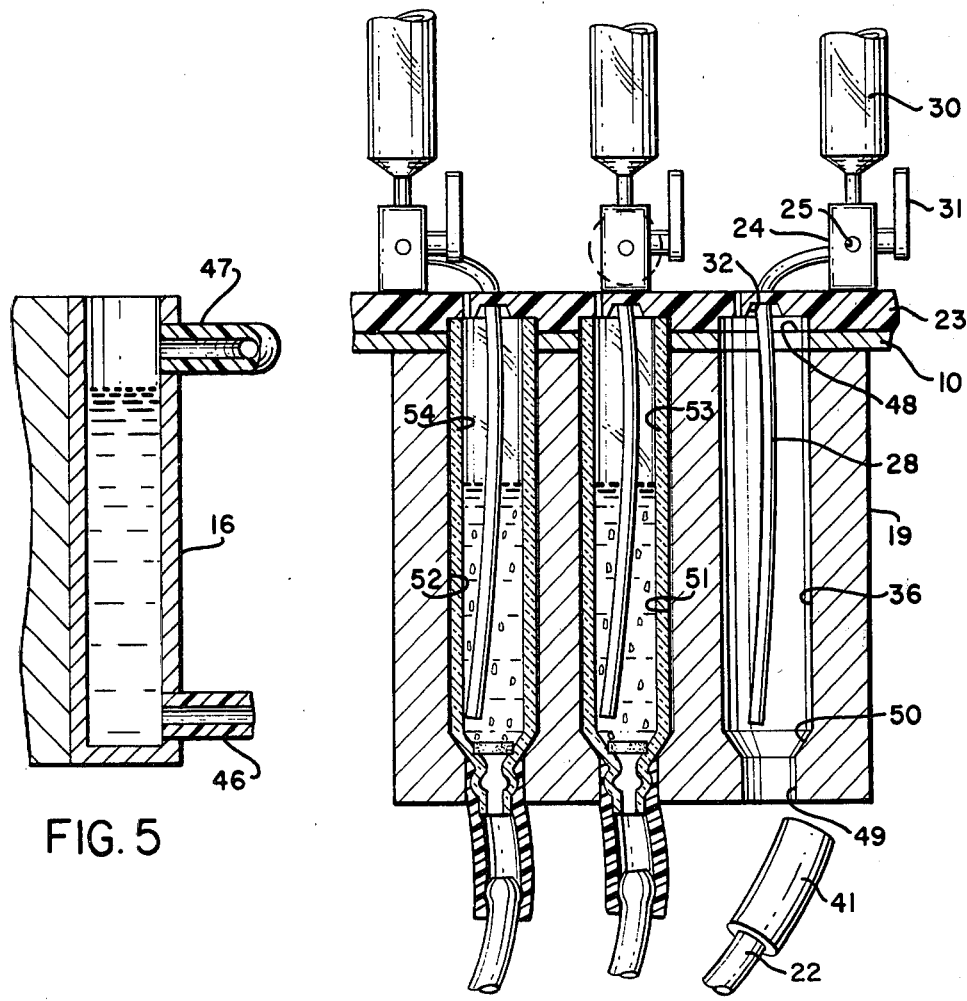
FIG. 5
FIG. 6

EQUILIBRATING INSTRUMENT FOR PREPARING QUALITY CONTROL SOLUTIONS

FIELD OF THE INVENTION

This invention relates to an improved equilibrating instrument or tonometer for preparing quality control solutions primarily useful in calibrating blood gas analyzers.

BACKGROUND OF THE INVENTION

Blood gas analyzers have become a widely used tool for clinical decision making. Essentially, a blood gas analyzer will measure the gas tension (partial pressure) in a given blood sample taken from a patient. For example, the amount of oxygen and carbon dioxide in a given blood sample might be respectively fifteen percent and seven percent. Analysis of such sample by the blood gas analyzer will reveal these values.

Because of protein contamination, electrode drift or simply plain human error, gas analyzers can become out-of-calibration and thus provide incorrect data. As a consequence, it is extremely important aside from legal liability considerations, for laboratory workers and the like to frequently check the blood gas analyzers and calibrate the same where necessary with quality control solutions.

With respect to the foregoing, it is known to provide ampules of blood or blood plasma or equivalent buffer solutions with known quantities of gas or gases such as oxygen and carbon dioxide, which can be broken open and used for quality control of the blood gas analyzer. However, these prepared solutions are relatively expensive. As a consequence, it has become the present day practice for various laboratories to use equilibrating instruments often referred to as tonometers for preparing quality control solutions as needed and at a fraction of the cost for previously prepared ampules. Essentially, these equilibrating instruments saturate blood or buffer solutions with precise amounts of single or mixed quality control gases (oxygen and/or carbon dioxide). The samples thus prepared are checked with automatic blood gas analysis systems. If the analyzer displays the predicted values for the sample, proper calibration has been verified.

U.S. Pat. No. 3,127,254 issued Mar. 31, 1964 contains a discussion of early prior art apparatus for equilibrating liquid and gas for providing quality control solutions. It is particularly directed towards an equilibration method as an alternative to the bubble type tonometers available at that time.

U.S. Pat. No. 4,256,461 issued from an application filed May 17, 1979 discloses a more recent method and apparatus for gas-liquid equilibration wherein the tonometry is carried out in a portable syringe structure utilizing a double chamber. This prior patent is significant in that it teaches the use of a heat block for providing a controlled environment for the diffusion tube wherein the equilibration is taking place. In this respect it is to be understood that proper partial pressures of the gas and liquid or blood sample can only be realized by providing a controlled temperature-pressure environment. The patentee not only teaches the use of a heat block for the diffusion tubes but shows that more than one diffusion tube can be incorporated in a single heat block thereby permitting multiple samples to be equilibrated simultaneously in a common controlled environment.

U.S. Pat. No. 4,251,483 filed Oct. 9, 1979 teaches a specific multiple independent path bubble type equilibrating apparatus or tonometer. In this particular instrument, three equilibrating operations can be carried out simultaneously in a single identical environment which, in the illustrative examples set forth, constitutes a water bath chamber incorporating the three diffusion tubes. For proper control, the usual humidifiers for providing moisture in the gas and thereby avoiding drying out of samples are incorporated in the single environment as well as the various flexible tubing interconnecting the humidifiers with the diffusion tubes. In addition, an important feature of this latter mentioned patent is the fact that the diffusion tubes incorporate a specially designed "fret" or porous member for breaking up the incoming gas into tiny bubbles, the principal characteristic being that there is provided an annular space about the member and the lower walls of the diffusion tube.

While the foregoing described equilibrating instruments or tonometers function well, it is not possible to readily clean these instruments without having to effect a substantial dismantling of the various components. For example, many times the diffusion tubes will become contaminated as well as some of the interconnected plastic tubing. Since it is not possible to easily separate these components from the remaining structure particularly when the same are enclosed in a common uniform environment, the entire instrument is simply disposed of and a new one used. Moreover, many of the presently available instruments require auxiliary controls and the like for operating the same; for example, a means for controlling the gas flow rate or even simply turning on and off the gas. These operations must normally be carried out at the gas source such as a compressed tank of gas and can result in some inconvenience in the preparation of a quality control solution.

Still another problem that can arise with presently available instruments involves those types wherein a side arm is provided on the diffusion tube to permit withdrawal of a sample after equilibration has been completed. By using such a side arm arrangement, it is indeed possible to select a sample fairly close to the portion of the solution wherein it can be assured equilibration has been completed. Such would have an advantage over simply attempting to withdraw a sample from the top of the diffusion tube. On the other hand, if the diffusion tube has to be replaced, the entire side arm mechanism must be replaced along with it. Provision of such a side arm which is also in at least part of the controlled environment makes it very difficult to provide any type of replaceable diffusion tube.

BRIEF DESCRIPTION OF THE PRESENT INVENTION

With all of the foregoing considerations in mind, the present invention contemplates the provision of an improved equilibrating instrument for preparing quality control solutions wherein the foregoing problems, associated with some prior art instruments, are avoided.

More particularly, in its broadest aspects, the instrument of the present invention provides for a unique arrangement of a humidifier for receiving and humidifying gas, a diffusion tube, flexible tubing connecting the gas from the humidifier to the diffusion tube and a temperature controlled environment for the diffusion tube such that either or both the flexible tubing and diffusion tube can be readily removed and replaced by new tubing and a new diffusion tube without disturbing the other components of the system. This arrangement is possible by utilizing a metal heat block rather than a water controlled environment wherein the heat block has a cavity with an open top for receiving the diffusion tube. Rather than any side arm arrangement, a valve block carrying an appropriate valve body with a downwardly extending sample receiving tube is positionable over the top opening in the heat block so that samples can be selected without requiring any side arm or the like. Further, the humidifier and plastic tubing connecting the humidifier to the diffusion tube are exterior of the heat block so that this plastic tubing can easily be replaced should it become contaminated.

In the preferred embodiment of this invention, the heat block is provided with additional cavities for receiving additional diffusion tubes each individually supplied with gas through its own humidifier and its own gas source. Further, individual valve bodies with sample tubes are provided for the additional cavities so that respective samples can be withdrawn from the top. This multiple arrangement permits more than one quality control solution to be prepared simultaneously.

BRIEF DESCRIPTION OF THE DRAWINGS

A better understanding of this invention will be had by now referring to the accompanying drawings in which:

FIG. 4 is a plan cross section of the instrument, taken in the direction of the arrows 4—4 of FIG. 3;

FIG. 5 is a fragmentary cross section taken in the direction of the arrows 5—5 of FIG. 4; and FIG. 6 is a fragmentary cross section taken in the direction of the arrows 6—6 of FIG. 4.

DETAILED DESCRIPTION OF THE PREFERRED EMBODIMENT

Figure 1:
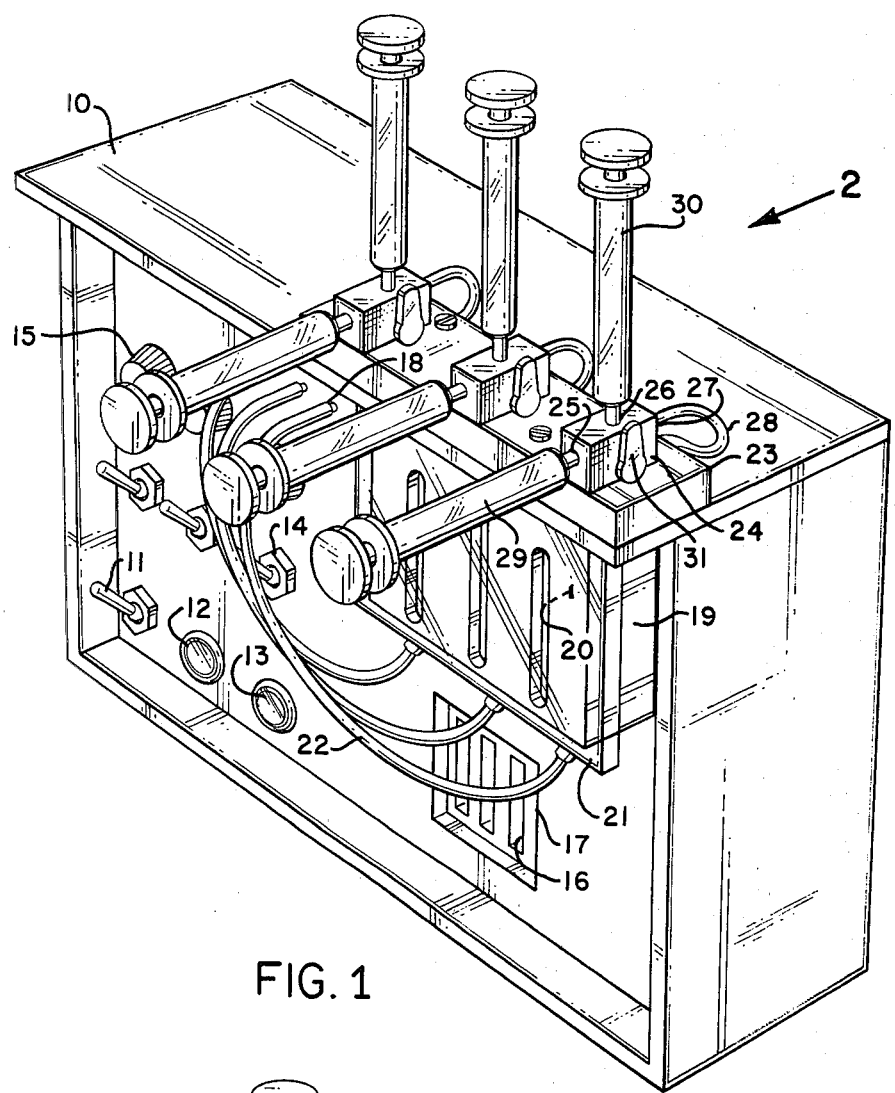
FIG. 1 is an overall perspective view of the improved equilibrating instrument of this invention.

Referring first to the upper left portion of FIG. 1, the instrument includes a housing 10 having a front control panel including various switches and indicators. Shown at the lower left, for example, is an on/off power switch 11, a power pilot light 12 and a heater pilot light 13. Pilot light 12 will indicate that power has been turned on and pilot light 13 will indicate than an appropriate thermostatically controlled heating means is operative for purposes of maintaining a controlled environment during the equilibration process, all as will become clear as the description proceeds.

In the particular embodiment illustrated in FIG. 1, the housing 10 is designed for enabling three equilibration operations to be carried out simultaneously; that is, three different quality control solutions can be prepared at the same time. Since the basic components for preparing each solution are essentially identical, a detailed description of one will suffice for all.

Still referring to the control panel on the upper left of FIG. 1, there is shown an on/off manually operable switch 14 for turning on or shutting off gas introduced into the rear of the housing 10. Also shown is a control knob 15 above the on/off switch 14 for controlling the flow rate of such gas.

Similar switches and flow control knobs are shown for the other two units.

Referring now to the lower right portion of FIG. 1 there is indicated at 16 a humidifier tube visible behind a window 17 which receives gas from the gas inlet on the rear of the housing 10 and moisturizes this gas. From the humidifier 16, the gas passes to a humidifier outlet shown in the upper central front portion of FIG. 1 at 18 adjacent to the flow control knob 15.

To the upper right of the front panel in FIG. 1 there is shown a heat block 19 incorporating a diffusion tube 20 visible through an open front portion on the heat block as will also become clearer as the description proceeds. A protective transparent plastic cover 21 overlies the open portion of the heat block 19 but will permit observation of the diffusion tube 20 behind the open portion.

Humidified gas from the humidifier 16 within the housing 10 passes to the humidifier outlet 18 adjacent to the flow control knob 15 to the bottom portion of the diffusion tube within the heat block 19 by way of a flexible gas conveying tubing. It will be noted that this tubing 22 is exterior of the housing 10 as are the corresponding gas conveying tubings for the other two units.

Referring now to the upper portion of FIG. 1, there is shown a valve block 23 positionable on top of the housing 10 to overlie the upper open end of the diffusion tube 20. This valve block includes a valve body 24 having first, second and third ports 25, 26 and 27. A sample selecting tubing 28 connects to the third port 27 and is positioned to extend under the rear portion of the valve block 23 downwardly into the open top of the diffusion tube 20. This arrangement will also become clearer as the description proceeds.

Connected to the first and second ports 25 and 26 of the valve body 24 are first and second syringes 29 and 30. A manually operable valve member 31 extends into the valve body 24. This valve member is designed to connect the first and third ports 25 and 27 together when in a first position and to connect the second and third ports 26 and 27 when in a second position.

Additional similarly designed valve bodies and syringes are provided for the other two units as shown in FIG. 1.

Figure 2:
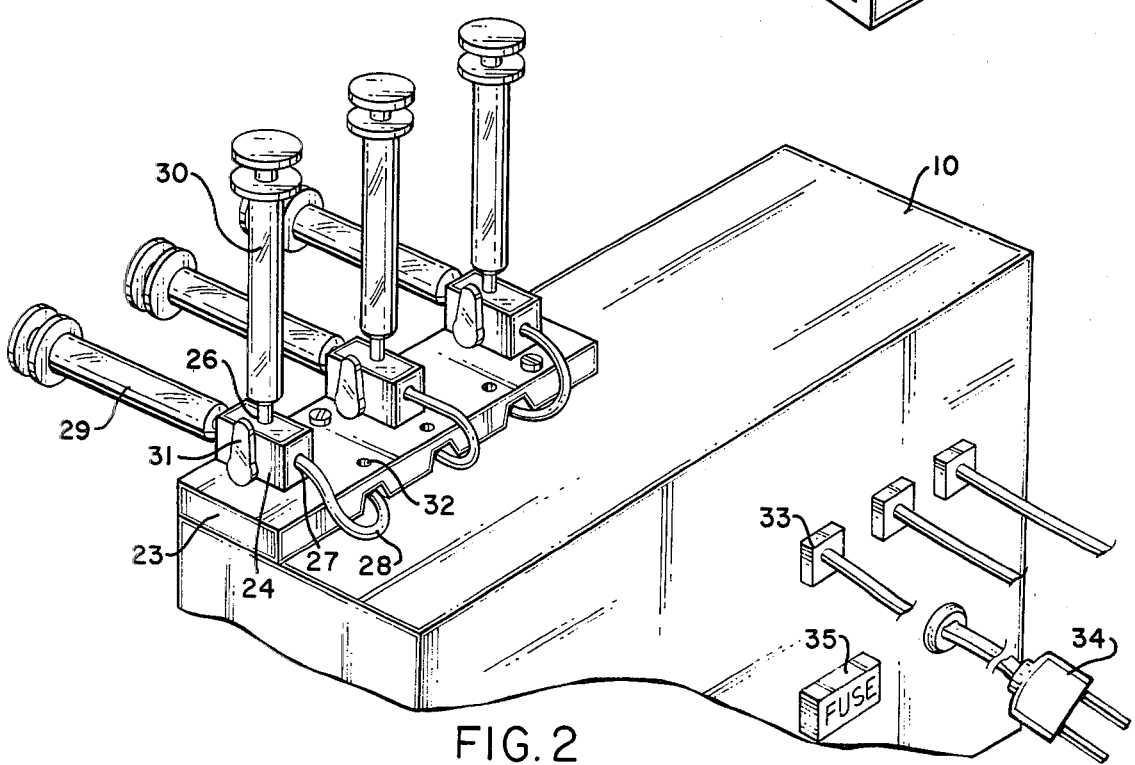
FIG. 2 is a fragmentary rear perspective view of the instrument looking in the direction of the arrow 2 of FIG. 1.

Referring to the rear view of FIG. 2, the manner in which the sample tubing 28 extends from the third port 27 of the valve body 24 under the valve block 23 will be evident. It will be noted that the valve block 23 includes a top vent opening 32 which actually overlies the top of the diffusion tube 20 described in FIG. 1 within the heat block 19 so as to provide an outlet passage for the gas bubbling through the diffusion tube.

In the lower right portion of FIG. 2, there is shown a gas inlet 33 for the various components described in FIGS. 1 and 2, similar independent gas inlets being provided for the other two units. Also shown is a power plug 34 and electrical fuse 35.

Figure 3:
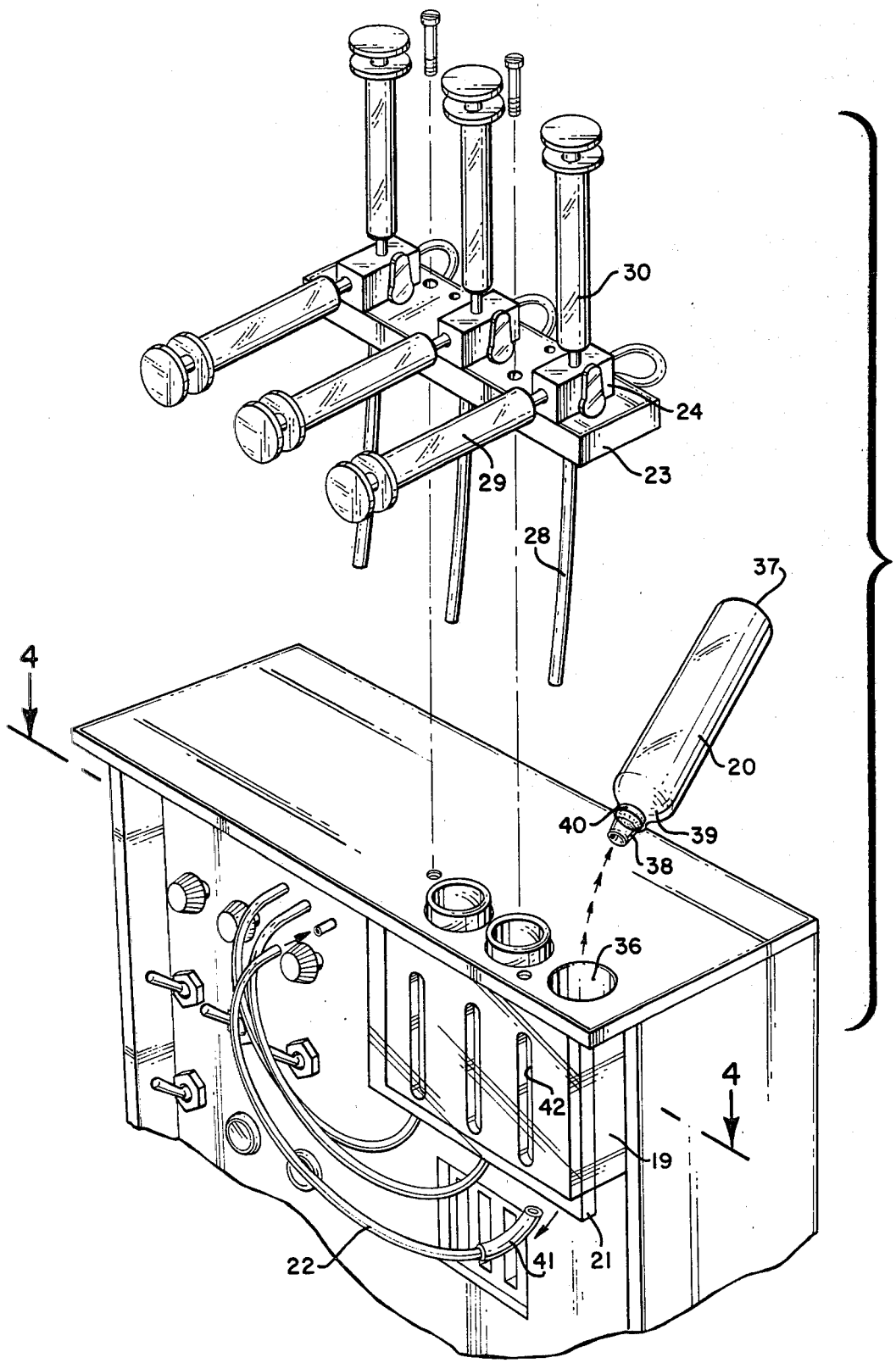
FIG. 3 is an exploded fragmentary perspective view of the instrument of FIG. 1 useful in explaining important features of the present invention.

Referring now to FIG. 3, the important features of the present invention are graphically illustrated. In FIG. 3, the valve block 23 has been removed from the top of the housing 10 by simply removing two hold-down screws or any other appropriate temporary securing means. It should be understood that removal of the valve block 23 is very easily carried out and can be accomplished without disturbing any of the other components.

With the valve block 23 raised as indicated, the sample tubing 28 from the valve body 24 will simply extend downwardly as shown, the same being free of the diffusion tube 20. In the particular showing of FIG. 3, this diffusion tube 20 has been shown removed from a cavity indicated at 36 in the heat block 19 to indicate that the diffusion tube can readily be dislodged and replaced after cleaning or replaced with a new diffusion tube.

Considering in detail the diffusion tube 20 shown in FIG. 3, the same has an open top 37 and terminates at its lower end in a gas inlet nipple 38 defining an external downwardly facing annular shoulder 39. A diffuser means in the form of an integrally formed disc 40 for even a separate porous member in the reduced diameter portion of the diffusion tube 20 is shown. This diffusion means 40 will break up gas entering into the diffusion tube through the nipple 38 so that small bubbles are generated which pass through the liquid sample placed in the tube.

With respect to the foregoing, it will be understood that when the diffusion tube 20 is received in the heat block cavity 36, the nipple 38 is exposed at the bottom exterior of the housing for receiving the flexible gas conveying tubing 22. In FIG. 3, this particular piece of tubing 22 is shown disconnected from the humidifier outlet 18 on the front panel and from the diffusion tube. A connector 41 permits connection of the tubing 22 to the nipple 38 on the diffusion tube in question and provides for easy manual disconnection from this tube.

From FIG. 3, it will thus be seen that either or both the diffusion tube and connecting tubing can be easily separated and disposed of or replaced after cleaning without affecting other components of instrument. The open portion in the heat block 19 permitting observation of an elongated lateral area of diffusion tube 20 is indicated at 42 in FIG. 3.

Referring now to the top plan cross section of FIG. 4, various internal connections for the gas flow path within the housing 10 will become clear. As in the case of the exterior components described in FIGS. 1 through 3, only one of the paths for the gas flow for the one diffusion tube 20 will be described, since the others are identical.

In FIG. 4 referring to the upper portion, the inlet gas line 33 is shown connecting through an on/off valve 43 operable by the referred to on/off toggle switch 14 on the front panel. From the on/off valve 43, inlet gas will pass through flexible tubing 44 to a needle valve 45 manually controllable by the knob 15 as described heretofore. From needle valve 45, flexible tubing 46 carries the gas to the lower end of the humidifier tube 16 and finally from the top of this humidifier the humidified gas passes through tubing 47 to the humidifier outlet 18 on the front of the panel.

In FIG. 4, the gas conveying flexible tubing 22 again is shown disconnected from its normal connection points merely to illustrate the ease with which the tubing can be removed and replaced.

Since the diffusion tube 20 is shown separated from the heat block in FIG. 3, for accuracy it has not been illustrated in the cross section of FIG. 4. However, the heat block cavity itself is clearly illustrated at 36 together with the removed lateral front portion 42 so that any diffusion tube received within the cavity will be readily visible from the front of the housing through the protective transparent sheet 21.

FIG. 5 illustrates in greater detail the humidifier tube 16 with its inlet tubing 46 and outlet tubing 47 described in FIG. 4. The sole function of the humidifier 16 is simply to add moisture to the incoming gas before the gas is passed to the diffusion tube. If the gas passes to the diffusion tube in a dry state, it will adversely affect the sample.

Referring now to FIG. 6, there is shown in greater detail the heat block 19 with its cavity 36. Again, the diffusion tube 20 shown in FIG. 3 is absent in order that the details of the heat block cavity can better be described.

Essentially, the cavity 36 is in the form of a vertical circular bore having an open top 48 over which the valve block 23 normally lies as described heretofore. The lower end of the cavity 36 terminates in a decreased diameter bottom opening 49 defining an internal upwardly facing annular shoulder 50. This shoulder 50 will engage the exterior downwardly facing annular shoulder 39 at the lower end of the diffusion tube 20 described in FIG. 3 to properly support the diffusion tube in the heat block 19. As described, however, the diffusion tube can readily be removed simply by disconnecting the connector 41 from the lower nipple and lifting the tube out the upper opening 48 of the cavity after the valve block 23 has been removed from the housing 10.

In FIG. 6, there are shown in the heat block 19 additional cavities 51 and 52 for the other two units. Shown disposed within the cavities 51 and 52 are the additional diffusion tubes 53 and 54. As also described heretofore, there is provided for each of the additional diffusion tubes an individual gas inlet, on/off gas switch control, gas flow control valve, humidifier, gas conveying tubing and valve block with first and second syringes. The arrangement is such that additional quality control solutions can be prepared simultaneously the same as the quality control solution prepared in the first described diffusion tube.

Operation

As an example of the operation of the present invention, assume it is desired to quality control a blood gas analyzer over a given range of blood gases. Typically, a gas mixture of five percent carbon dioxide, twelve percent oxygen and the remainder nitrogen is introduced into the first gas inlet 33 shown in FIG. 2 for equilibration with a liquid such as blood or a blood plasma placed within the diffusion tube 20. Typically, there might be provided about six cc. of liquid in the diffusion tube 20, this liquid being introduced, for example, by means of the first syringe 29 with the valve member 31 in its first referred to position so that the liquid can pass down through the sampling tubing 28.

A second gas mixture of, for example, seven percent carbon dioxide, fifteen percent oxygen and seventy-eight percent nitrogen is introduced into a second gas inlet on the rear of the housing 10 to be equilibrated with a sample of liquid, such as blood or blood plasma received in the diffusion tube 53 illustrated in FIG. 6. Finally, a third gas mixture of, for example, eight percent carbon dioxide, twenty-one percent oxygen and seventy-one percent nitrogen is introduced into the third gas inlet for equilibration with a liquid sample in the third diffusion tube 54 described in FIG. 6.

Prior to introduction of any of the samples into the diffusion tubes, the equipment is first turned on by the power switch 11. The pilot light 12 indicates that energy is being supplied. When the pilot light 13 is on, it is an indication that the heat block 19 is being properly heated and maintained at a constant temperature. This temperature is typically 37° C., corresponding to the temperature of blood circulating in a human body. As stated, this temperature is automatically maintained by an appropriate thermostatically controlled circuit in the housing 10.

The three on/off switches, such as the switch 14, in FIG. 1 are now turned to their "on" positions so that gases entering the respective tubings will pass through the three individual humidifiers illustrated in FIG 4. These humidifiers can be observed through the window 17 in FIG. 1, the presence of bubbles in the humidifiers indicating that gas is properly flowing. In this respect, the rate of gas flow can be adjusted by the control knobs such as the knob 15. This gas, after being humidified will pass out the gas outlets such as the gas outlet 18 through the exterior flexible tubing into the lower ends of the three diffusion tubes within the heat block 19.

With the gas flowing as described above, the blood plasmas samples are now introduced into the diffusion tubes as described heretofore, the gas flow preventing the samples from passing out the lower ends of the tubes. The gas will be broken into small bubbles by the respective diffusion members in the lower portion of the diffusion tubes to bubble up through the liquid sample. The vents such as the vent 32 in the valve block 23 permit escape of gas out the top of the tubes and the valve block.

After it is assured that the liquid samples with the gases bubbling therethrough have attained the temperature of the heat block 19, an equilibration time period is started.

It might take typically, for example, about forty minutes for equilibration to be completed; that is, for the absorption of the respective ratios of gases into the blood sample.

After equilibration is completed, a small "dead sample" is withdrawn from the diffusion tube into the first syringe such as the syringe 29 shown in FIG. 1 with the valve member 31 in its first position. The valve member 31 is then turned to its second position and a second sample of the prepared quality control solution is drawn into the second syringe 30. By this arrangement, any portion of the liquid which has not been completely saturated and which might be disposed within the sample tube 28 is first removed by the syringe 29 so that the second sample selected by the syringe 30 with the valve member 31 in its second position will constitute a proper quality control solution. This second sample in the syringe 30 can then be transferred to the blood gas analyzer for quality control purposes and a determination made as to whether the analyzer provides a readout corresponding to the partial pressures of the carbon dioxide and oxygen known to exist in the sample as a consequence of the equilibration.

Second and third samples in the diffusion tubes 53 and 54 shown in FIG. 6 are similarly withdrawn and used in calibrating the blood gas analyzer so that the accuracy of the analyzer can be determined over a range of different partial pressures of the carbon dioxide and oxygen in the blood samples.

Should the flexible tubing extending from the outlets of the humidifier into the bottom portions of the diffusion tubes become contaminated as might be caused by settling back of blood or blood plasma in a diffusion tube into the connected tubing, the tubing itself can readily be disconnected as described for the tubing 22 from the front of the panel and the bottom of the diffusion tube at the lower end of the heat block and discarded. New tubing can then be used to replace this contaminated tubing.

Similarly, after an equilibration has been completed, the diffusion tubes themselves can readily be removed and cleaned or even disposed of if damaged for any reason by simply removing the valve block 23 as illustrated in the exploded view of FIG. 3 and lifting the tubes out by hand.

It will be noted that the tonometer path of gas flow through the humidifier and into the entrance of the diffusion tubes is largely exterior of the temperature environmental control in the form of the heat block 19. On the other hand, the critical sample itself is maintained at the proper constant temperature by the heat block.

Because of the foregoing arrangement, and as set out heretofore, it is very easy to change the gas flow tubing as required.

Further, it will be noted that rather than using side arms and the like extending from the diffusion tubes, a sample is withdrawn from the open top of the tube by means of the downwardly depending sampling tubes such as 28 from the valve block 23. By this arrangement, it is very easy to simply remove the diffusion tube itself since the same is uncluttered by the presence of side arms and the like.

It can be appreciated from all of the foregoing that the present invention thus provides a greatly improved equilibrating instrument for preparing quality control solutions having unique advantages not available heretofore in the prior art.

We claim:

1. In an equilibrating instrument for preparing quality control solutions of a liquid and gas, including a humidifier for receiving and humidifying gas, a diffusion tube, flexible tubing connecting the gas from the humidifier to the diffusion tube and a temperature controlled environment for said diffusion tube, the improvement including providing said temperature controlled environment by means of a metal heat block having a cavity open at the top for receiving said diffusion tube, the lower end of the cavity having a bottom opening of reduced diameter to define an upwardly facing annular shoulder to support said diffusion tube, and wherein said humidifier and flexible tubing are exterior of the heat block with one end of the tubing connecting to the humidifier and the other end extending to the bottom opening of said heat block to connect to said diffusion tube whereby either or both the diffusion tube and connecting tubing can be easily separated and disposed of without affecting other components of the instrument.

2. An instrument according to claim 1, in which said heat block includes at least one additional cavity of the same type as said first mentioned cavity for holding an additional diffusion tube so that two quality control solutions can be prepared simultaneously.

3. An instrument according to claim 1, in which said improvement further includes a valve block positionable over the top opening of said cavity having a valve body with first, second and third ports and a sample selecting tube connected to the third port and positioned to extend under the valve block downwardly into the open top of said diffusion tube; first and second syringes connected to said first and second ports; and a manually operable valve member extending into said valve body for connecting said first and third ports together when in a first position and connecting said second and third ports together when in a second position whereby equilibrated liquid and gas forming said quality control solution can be withdrawn after first withdrawing a dead sample with said first syringe with the valve member in the first position by said second syringe when the valve member is thereafter placed in a second position.

4. An equilibrating instrument for preparing quality control solutions of a liquid and gas including, in combination:

(a) a housing having at least one gas inlet for connection to a source of compressed gas;

(b) at least one humidifier in said housing for receiving gas from said inlet, said humidifier having an outlet connection on the exterior of said housing;

(c) a heat block secured to said housing and having at least one elongated vertical cavity open at the top and having a decreased diameter bottom opening to define an internal upwardly facing annular shoulder;

(d) thermostatically controlled means in said housing for maintaining said heat block at a given constant temperature;

(e) a diffusion tube having an open top and terminating at its lower end in a gas inlet nipple defining an external downwardly facing annular shoulder, said tube being receivable in said cavity with its downwardly facing annular shoulder seated on said upwardly facing annular shoulder of said cavity and its nipple extending through said bottom opening to a point exterior of said housing so that said tube is supported in said cavity and yet readily manually removable out the top of said cavity;

(f) a diffuser means in the lower portion of said diffusion tube;

(g) a flexible gas conveying tubing exterior of said housing connecting said humidifier outlet to said diffusion tube nipple so that gas can be passed from said humidifier upwardly through said diffusion tube; p1 (h) a valve block positionable on top of said housing to overlie the upper open end of said diffusion tube, said valve block including a valve body having first, second and third ports;

(i) a sample selecting tube connecting to said third port and positioned to extend under the valve block downwardly into the open top of said diffusion tube to terminate close to said diffusion means;

(j) first and second syringes connected to said first and second ports; and (k) a manually operable valve member extending into said valve body for connecting said first and third ports together when in a first position and connecting said second and third ports together when in a second position whereby a liquid to be equilibrated with gas can be injected into said diffusion tube by said first syringe with said valve member in said first position and gas passed into said diffusion tube and through said diffusion means to bubble up through said liquid until equilibration at said given temperature is completed and thereafter, a small "dead sample" withdrawn into said first syringe and said valve member then turned to its second position to permit withdrawal of a sample of the prepared quality control solution into said second syringe for quality control purposes, and whereby said flexible gas conveying tubing can be easily disconnected after equilibration if it should be damaged or contaminated and replaced without disassembling other component parts of the instrument and whereby said diffusion tube itself can be removed and disposed of or easily cleaned and replaced without affecting other components by simply lifting off said valve block and removing the tube out the open top of said cavity.

5. An instrument according to claim 4, in which said cavity in said heat block includes a lateral opening rendering a side part of said diffusion tube visible from the exterior of said housing and in which the housing further includes a window means for enabling observation of said humidifier so that an operator can readily observe the gas flow through the humidifer and diffusion tube.

6. An instrument according to claim 4, including a manually operable on/off control valve connected at said gas inlet for enabling shutting off of said gas into the humidifier.

7. An instrument according to claim 4, including a manually operable gas flow rate control means in said housing connected between said gas inlet and said humidifier to control the flow rate of said gas.

8. An instrument according to claim 4, in which said heat block includes additional cavities for receiving additional diffusion tubes, there being provided an individual gas inlet, on/off valve, flow control valve, humidifier, gas conveying tubing, a valve body on said valve block and first and second syringes for each of said additional diffusion tubes so that additional quality control solutions can be prepared with different gas ratios simultaneously with said first mentioned quality control solution.

* * * * *